(12) United States Patent
Gueret

(10) Patent No.: US 6,645,172 B1
(45) Date of Patent: *Nov. 11, 2003

(54) DEVICE AND METHOD FOR NASAL INHALATION

(75) Inventor: Jean-Louis H. Gueret, Paris (FR)

(73) Assignee: L'Oreal S.A., Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/166,420

(22) Filed: Oct. 5, 1998

(30) Foreign Application Priority Data

Oct. 3, 1997 (FR) .......................................... 97 12349

(51) Int. Cl.$^7$ .......................... A61M 11/00; A61M 51/08
(52) U.S. Cl. ................................. 604/93.01; 128/204.12
(58) Field of Search ............................ 604/93, 94, 77, 604/890.1, 23, 304; 128/204.11, 204.12, 204.13, 204.14, 203.29; 239/36, 54, 56, 60; 222/173, 175, 187, 575; 221/185; 63/DIG. 2

(56) References Cited

U.S. PATENT DOCUMENTS

| | | | | |
|---|---|---|---|---|
| 270,655 A | * | 1/1883 | Fruhling, Jr. .......... | 128/205.29 |
| 406,118 A | * | 7/1889 | Welch .................... | 128/204.11 |
| 1,218,906 A | * | 3/1917 | Sheperd ................. | 128/204.12 |
| 2,560,681 A | * | 7/1951 | Berkowitz .................... | 299/24 |
| 3,784,102 A | * | 1/1974 | Stults .......................... | 239/36 |
| 3,788,296 A | | 1/1974 | Klatt et al. | |
| 3,823,873 A | * | 7/1974 | Miller, Jr. et al. ............. | 239/54 |
| 3,828,577 A | * | 8/1974 | Haynes ............................. | 63/2 |
| 4,285,468 A | * | 8/1981 | Hyman ......................... | 239/55 |
| 4,293,602 A | * | 10/1981 | Coffey et al. ................. | 428/28 |
| 4,817,868 A | * | 4/1989 | Cook et al. .................... | 239/55 |
| 4,874,129 A | * | 10/1989 | DiSapio et al. ............... | 239/36 |
| 4,955,945 A | | 9/1990 | Weick | |
| 5,538,013 A | * | 7/1996 | Brannon ..................... | 128/857 |
| 5,636,787 A | * | 6/1997 | Gowhari ...................... | 239/36 |
| 5,678,763 A | * | 10/1997 | Scheuer et al. ............... | 239/54 |

FOREIGN PATENT DOCUMENTS

| | | |
|---|---|---|
| CH | 492 458 | 6/1970 |
| FR | 0 945 897 | 5/1949 |
| FR | 2 654 002 | 5/1991 |
| GB | 0 520 491 | 4/1940 |
| WO | WO 88/01884 | 3/1988 |

OTHER PUBLICATIONS

EPO Search Report for EP 0 906 765 A1.
English Language Derwent Abstract of FR 2 654 002.

* cited by examiner

*Primary Examiner*—Michael J. Hayes
(74) *Attorney, Agent, or Firm*—Finnegan, Henderson, Farabow, Garrett & Dunner, LLP

(57) ABSTRACT

An inhalation device includes at least one support containing a product including at least one active substance. The support is able to release, in the form of emanations, a volatile phase of the active substance. Attachment elements are provided to permit attachment of the device to at least one point situated near the nostrils to permit nasal inhalation of the emanations. The support and the attachment elements are configured so that the emanations when leaving the support are not aimed directly towards the nostrils and travel a distance before coming in contact with the nostrils or the nasal mucosa. Also disclosed is a method of inhalation treatment using the device.

2 Claims, 3 Drawing Sheets

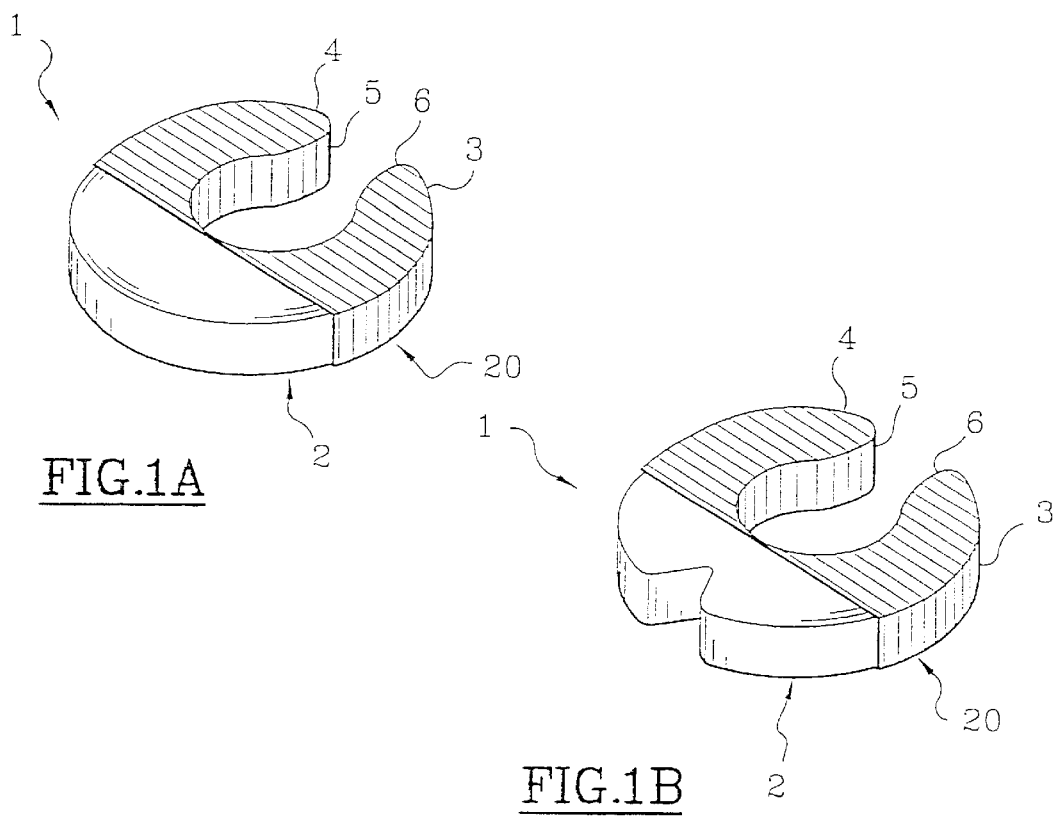
FIG.1A
FIG.1B
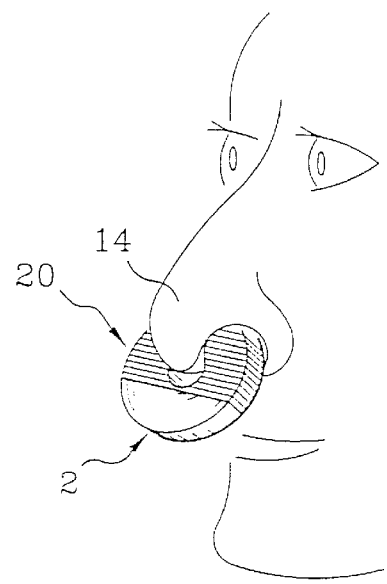
FIG.2

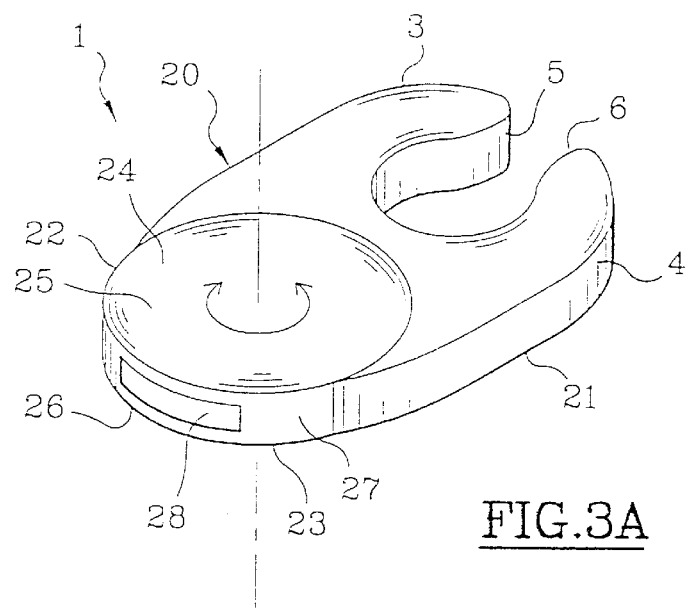
FIG.3A
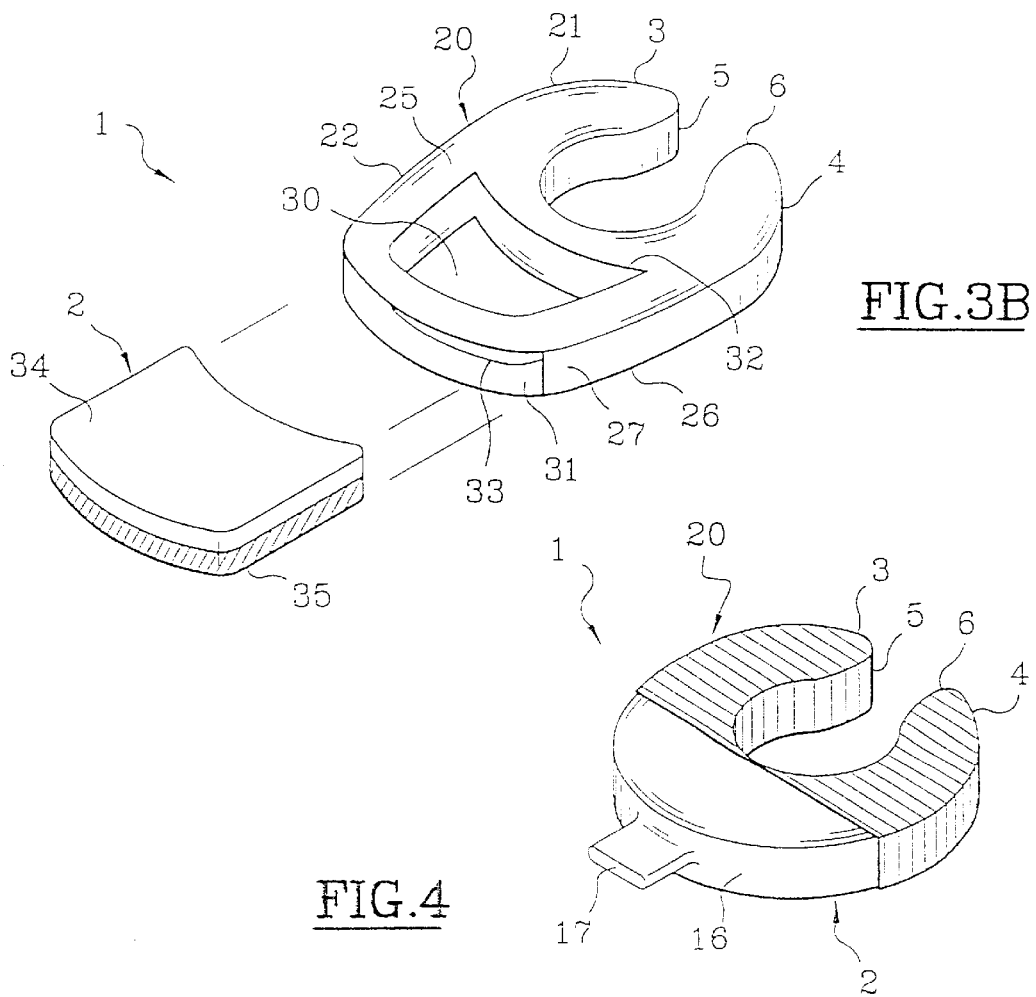
FIG.3B
FIG.4

DEVICE AND METHOD FOR NASAL INHALATION

The present invention relates to a device and method for nasal inhalation of substances having an activity, in particular against stress or against allergies, or an ability to assist in breathing.

More particularly, the present invention relates to a device capable of being attached to part of the nose in such a way as to release one or more active substances, for nasal inhalation, in the form of volatile emanations localized in proximity to the nostrils.

Inhalation devices have been described in FR-A-945,897, GB-A-520,491 or U.S. Pat. No. 3,788,296. In all these devices, the support containing the active substances is always arranged inside the nostrils, even in contact with the nasal mucosa, or directly opposite the nostrils, i.e., the active substance when leaving the support is aimed directly towards the nostrils. Some of these devices are intended to be used on animals. One of the problems resulting from the use of these devices lies in the fact that the emanations, oriented directly inside the nostrils and/or aimed directly towards the nostrils, can aggravate the nasal mucosa and can inconvenience the person wearing the device. The problem is particularly noticeable when the device contains aromatic substances whose scent can be very powerful. In addition, there may be problems of allergic or inflammatory reactions on account of the presence of these active substances being too close to the nasal mucosa.

In light of the foregoing, there is a need in the art for an improved inhalation device.

Accordingly, the present invention is directed to an inhalation device that substantially obviates one or more of the limitations of the related art. In particular, the present invention is preferably directed to a device of reduced size which can be worn without any appreciable inconvenience to the person wearing it, in particular at night, when lying down.

Another preferred object of the invention is to make available a device which is able to permit aromatherapy using substances, in particular based on essential oils, containing in particular camphor, eucalyptus, thyme, lavender or lily of the valley, which can have an action against stress or against allergies, an action on breathing, or any other action aimed at improving the comfort of the person who is wearing it.

One other preferred object of the invention is to provide a device having a reloadable structure.

A further preferred object of the invention is to provide a device which is easy and economical to make, and which permits a controlled flow rate of the inhaled emanations.

It should be understood that the invention could still be practiced without performing one or more of the preferred objects and/or advantages set forth above. Still other objects will become apparent after reading the following description of the invention.

To achieve these and other advantages and in accordance with the purpose of the invention, as embodied and broadly described herein, the invention includes an inhalation device comprising at least one support containing a product including at least one active substance. The support is able to release, in the form of emanations, a volatile phase of the active substance. Attachment elements are provided to permit attachment of the device to at least one point situated near the nostrils to permit nasal inhalation of the emanations. The support and the attachment elements are configured so that the emanations when leaving the support are not aimed directly towards the nostrils and travel a distance before coming in contact with the nostrils or the nasal mucosa.

In one aspect of the invention, a device is provided which automatically stays in place on the nose, allowing the user to carry out other activities at the same time. Preferably, the device is remarkably comfortable, and no part of the support able to directly release emanations is arranged inside the user's nostrils. In practice, the support preferably is arranged sufficiently close to the nostrils to allow the nasal breath, by means of its warmth, to promote the release of the emanations. However, the emanations are not directly in contact with the nostrils or nasal mucosa, nor are they oriented directly opposite the nostrils, i.e., the emanations when leaving the support are not aimed directly at the nostrils, so as not to inconvenience the user. Good results have been obtained with the "emanating" part of the support located approximately 1 to 2 cm from the nasal orifices. This is particularly useful when the support contains essential oils, whose scent is relatively aggressive, or other active substances whose contact with the nasal mucosa or nostrils could trigger allergic or inflammatory reactions.

Within the meaning of the present invention, the term "active substance" defines a compound having either a therapeutic activity (treatment of stress, allergy, breathing, or sleep) or a comforting action (in particular by way of scents or perfumes).

As has been mentioned above, the support is preferably maintained in proximity to the nostrils, in particular above or below them, so that the warm air of respiration, in addition to the normal temperature of the body of the person wearing it, is able to promote the volatile emanations which are then inhaled by the nasal route. Preferably, the inhalation is permanent and, once the device is in place on the nose, no particular manipulation is needed.

In another aspect of the invention, the attachment elements are advantageously at least one portion of a body able to receive the support. This version affords a great many possibilities in terms of comfort, reloading of the device, metering the flow rate of the emanations, reusing the device, etc.

According to one preferred embodiment, the device includes two arm portions forming a clip. A first end of each arm is integral with the device, and a second end of each arm is free. The second free ends are spaced apart from one another and define a gap able to permit attachment of the device to the bridge of the nose, to the nasal cartilage (septum), or to at least one of the side walls defining the nostrils. The arm portions are preferably able to spread apart elastically during attachment of the device. The clip is preferably a portion of a body inside which the support is mounted. The profile, and the surfaces of the clip contacting the user during attachment, are chosen in such a way as to provide the maximum comfort for the user.

According to a preferred embodiment, the device has, essentially opposite to a median point of the gap defined by the second ends, a notch which is able to confer greater elasticity to the arm portions. This increases the hold of the device on the nose, the ease of fitting and removing the device, and the comfort which it provides.

In yet another aspect of the invention, the body preferably has a recess able to receive the support. The body is preferably made of a material impervious to the emanations, and includes at least one opening to allow the emanations to pass through. Thus, it is possible to localize the emanations in a very precise manner so as not to inconvenience the user. This, in particular, avoids the emanations from being inhaled directly from the support, which, especially with certain highly aromatic substances, can be particularly uncomfortable.

In still another aspect, the support may be mounted in a removable manner in the recess to form a reloadable structure. The body may thus be reused many times by simply changing the cartridge formed by the support. The device may be marketed in the form of a kit including a reloadable body, and a plurality of refills containing, for example, several scents with identical or different actions. In this case, the body is preferably made of a washable material.

By way of example, the body is made of a material chosen from among polypropylenes, polyethylenes, polyvinyl chlorides, and natural, synthetic or thermoplastic elastomers.

According to one particular embodiment, the device forms a substantially flat structure which includes two main faces and an edge, and the opening is formed in one and/or the other of the main faces and/or in the edge. Several openings can be provided in such a way as to permit, in particular, a greater diffusion of the product, or else a satisfactory diffusion, irrespective of the position of attachment of the device on the nose. It is also possible for one of these openings to serve specifically for the insertion of a refill. In an alternative embodiment, the device contains two superposed supports, one of the supports diffusing through a first opening situated on a first face of the device, the other diffusing through a second opening arranged on the other face of the device. It is thus possible to produce "cocktails" of emanations with combined actions or scents.

According to one preferred embodiment, the position of the support in the recess may be adjusted in such a way as to modify the output rate of the emanations. By way of example, the edge includes an opening allowing the support to be inserted to a variable depth into the recess.

According to one variant, the support is in a fixed position in the recess, and the size of at least one opening is variable in such a way as to modify the output rate of the emanations. By way of example, the support has a structure including a base and a lid mounted for rotation on the base. The angular position of the base in relation to the lid determines the size of an opening formed either on the edge or on at least one of the main faces of the device.

According to another variant, the support includes an element defining a closed volume which can contain the product. The element is preferably obtained by blow-moulding a material which is permeable to the emanations. By way of example, the material is chosen from among low-density polyethylenes, flexible polyvinyl chlorides, copolymers of ethylene and vinyl acetate (EVA), etc. Advantageously, after blow-moulding, the volume is closed in the area of a localized zone serving as a means of gripping the device.

The support is preferably made of a porous material which is able to deeply absorb the product.

The material may be saturated with product, by saturation under vacuum, by swelling, by pressure, or by capillarity, and can be chosen from among NBR (natural butadiene rubber) or SBR (synthetic butadiene rubber) foams, elastomer foams, in particular of polyether block amide, polyurethane, or PEBAX®, felt, wool, cellulose, wood, terracotta, plaster, ceramics, etc.

The support may also be made up of a matrix consisting of a material chosen from among silicones, latices, polyurethanes, gums, etc.

According to certain embodiments, at least one of the faces of the support is covered with a sheet of material chosen from among polyethylenes, felt, etc. In this configuration, at least one of the sheets may be impervious to the emanations and may be peeled off so as to permit the passage of the emanations through the corresponding face of the support.

By way of example, the device forms a substantially flat structure and has a thickness of from about 0.5 mm to about 10 mm, preferably of from about 1 mm to about 8 mm, and still more preferably of from about 1.5 mm to about 5 mm and even more preferably from 0.5 mm to 10 mm, more preferably from 1 mm to 8 mm, and still even more preferably from 1.5 mm to 5 mm. The support may comprise one cut or moulded piece.

By way of example, the product contains an aromatic substance having a comforting or therapeutic activity, in particular an activity against stress or against allergies, or assisting in sleep or breathing.

In a further aspect of the invention, the product may be chosen from among essential oils, particularly based on camphor, eucalyptus, lavender, thyme or lily of the valley.

In an even further aspect of the invention, a method of inhalation treatment is provided. The method includes attaching the device to at least one location on a body (at least one location on a body of a human or other animal) situated near the nostrils. The method also includes releasing from the device, in the form of emanations, a volatile phase of the at least one active substance. The emanations released from the device are directed so that the emanations are not aimed directly towards the nostrils and travel a distance before coming in contact with the nostrils or the nasal mucosa.

In one aspect of the method, the attaching of the device includes placing a portion of the body between a pair of arms.

In another aspect of the method, the rate of release of the emanations from the device is adjusted.

In yet another aspect of the method, another support is loaded in the device, for example in place of an original support.

In an even further aspect of the method, the emanations are effective to provide at least one of stress relief, allergy treatment, comfort providing, breathing assistance, and sleep assistance.

Although the inhalation treatment method according to the invention is preferably practiced with the structure disclosed herein, it should be understood that the method according to the invention in its broadest sense is not so limited.

Besides the structural arrangements and method steps set forth above, the invention could include a number of other arrangements and method steps, such as those explained hereinafter. It is to be understood that both the foregoing general description and the following detailed description are exemplary, and are intended to provide further explanation of the invention as claimed.

The accompanying drawings are included to provide a further understanding of the invention and are incorporated in and constitute a part of this specification. The drawings illustrate embodiments of the invention and, together with the description, serve to explain the principles of the invention. In the drawings, FIG. 1A is a perspective view show a first embodiment of a device according to the invention;

FIG. 1B is a view similar to that of FIG. 1A showing a second embodiment of the device;

FIG. 2 is a view showing one way in which the device of FIG. 1A is attached to a user;

FIG. 3A is a view similar to that of FIG. 1A showing a third embodiment having a rotatable lid;

FIG. 3B is a view similar to that of FIG. 1A showing a fourth embodiment having a multiple layered support;

FIG. 4 is a view similar to that of FIG. 1A showing a fifth embodiment wherein the support is a closed volume element;

Figure 5A:
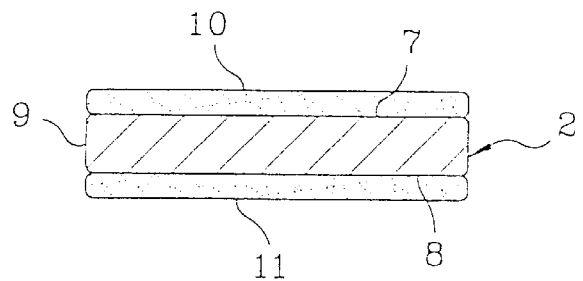
FIG. 5A is a cross-section view of an alternative support for use in the device.

Reference will now be made in detail to the present preferred embodiments of the invention, examples of which are illustrated in the accompanying drawings. Wherever possible, the same reference numbers are used in the drawings and the description to refer to the same or like parts having similar structural configuration(s) and/ or function (s).

FIGS. 1A shows a first embodiment of device 1 according to the invention, and FIG. 1B shows a second embodiment similar to that of FIG. 1A. In both of these embodiments, the device 1 is a substantially flat structure including a support 2 and attachment elements 3, 4. Preferably, the support 2 is formed by cutting or moulding material, and the attachment elements 3, 4 are a pair of arms. The support 2 forms a substantially closed loop having the arms 3, 4. The arms 3, 4 have free ends 5, 6 situated next to one another and are capable of attaching the device 1 on the nose 14. The part of the support 2 forming the attachment arms 3, 4 is arranged inside a thermo-formed shell 20 made of a material impervious to the emanations, so that when the device 1 is mounted on the nose in the manner shown in FIG. 2, the emanations are not oriented directly opposite (i.e., not aimed directly towards) or in contact with the nostrils. In other words, the support 2 and the attachment elements (arm) 3, 4 are configured so that the emanations leaving the support 2 are not aimed directly at the nostrils and travel a distance before coming in contact with the nostrils or the nasal mucosa. In addition, the support 2 is not arranged directly inside the nostrils and does not directly touch the nasal mucosa.

The support 2 is made of an elastically deformable material so as to allow the device 1 to be fitted in the manner illustrated in FIG. 2, by attachment to the septum or central cartilage separating the two nostrils. Alternatively, the support 2 may be attached to the side wall(s) of one or both of the nostrils. During fitting, the free ends 5, 6 of the arms 3, 4 spread apart elastically, and return to their attachment position by means of elasticity. The profile of the free ends 5, 6 of the arms 3, 4 is chosen in such a way as to provide maximum comfort during use. In practice, even a very low elasticity suffices.

The device 1 is preferably made of a porous material which is able to deeply absorb the product. The material can be saturated with product, by saturation under vacuum, by swelling, by pressure, or by capillarity. By way of example, the material is chosen from among NBR (natural butadiene rubber) or SBR (synthetic butadiene rubber) foams, elastomer foams, in particular polyether block amide, polyurethane, or PEBAX®.

The elasticity may result from the structure of the thermo-formed shell 20, the material forming the support 2, or may result from the elasticity of layers or sheets covering the two faces of the support 2. In the alternative support configuration shown in FIG. 5A, the support 2 is covered on each of its faces 7, 8 by a sheet 10, 11 of a material such as a polyethylene or a rubber, or felt. In addition to the elasticity which they may confer on the structure of the support 2, such sheets 10, 11, when they are impervious to the product contained in the support 2, make it possible to limit the diffusion of the product through only one edge 9 of the support 2, which may be desirable for certain highly aromatic products so as not to inconvenience the user. Moreover, these sheets 10, 11 make it easier to handle the support 2 impregnated with liquid product. In this configuration, in addition to the materials cited above, other materials may be used to produce the support containing the product to be inhaled. By way of example, it is possible to use a silicone matrix. This matrix may be rigidified by including a frame within it, such as a frame of cotton.

Figure 5B:
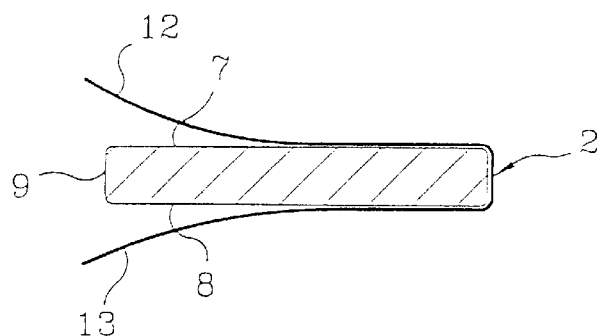
FIG. 5B is a view similar to that of FIG. 5A of another alternative support.

In the support embodiment shown in FIG. 5B, each of the faces 7, 8 of the support 2 is covered with a respective, peelable polyethylene sheet 12, 13. The sheets 12, 13 are removed before the first use. Alternatively, the two sheets 12, 13 are removed after a certain period of time during use of the device so that the product is initially diffused through only an edge of the support 2. The sheets 12, 13 also may be removed before insertion into the shell 20, either simultaneously, or one first, then the other after a further period of use when the diffusion via the edge 9, then via the first face, becomes insufficient.

In the embodiment of FIG. 1B, a notch 15 is provided in a portion of the support 2 located essentially opposite a median point of the gap defined by the second free ends 5, 6. The notch 15 provides greater elasticity for the arm portions 3, 4.

In the embodiment in FIG. 4, the support 2 is made up of an element 16 defining a closed volume, obtained in particular by blow-moulding, and containing, in liquid form, the product to be inhaled. After filling, the element 16 is closed in the area of a zone 17 situated opposite the free end 5, 6 of the arms 3, 4, in particular by high frequency welding.

The arms 3, 4 are each arranged inside a thermo-formed portion 20 made of a material impervious to the emanations, in such a way as to avoid any emanation being directly opposite (i.e., aimed directly towards) the nostrils. In the same way as in the embodiments in FIGS. 1A and 1B, attachment is carried out, when fitting the device, by slightly spreading apart the arms 3, 4 which recover their initial position by elastic memory, in such a way as to attach the device either to the bridge of the nose, to the septum of central cartilage defining the two nostrils, or to one of the lateral margins of one or both of the nostrils. The zone 17 advantageously serves as a means for gripping the device 1. The material used to produce the element 16 is chosen from among materials permeable to the volatile phase of the product contained in the element 16. Examples of materials that can be used are polyethylene, flexible polyvinyl chloride, or a copolymer of ethylene and vinyl acetate (EVA). Before use, the surface of the element 16 can be covered by an adhesive element which is impervious to the volatile phase.

In the embodiment in FIG. 3A, the support is contained inside a body 20 made of a material which is impervious to the volatile phase of the product to be inhaled. By way of example, a washable material is used, such as a polypropylene. In this embodiment, the body 20 includes two parts 21, 22. The first part 21 consists principally of the arms 3, 4 used for attaching the device 1 on the nose, in a manner identical to the other embodiments. The second part 22, fitted, for example, by being snapped onto the first part 21, forms a casing including a base 23 and a lid 24. The lid 24 is mounted to rotate freely with respect the base 23, and inside the casing there is a support of the type discussed with reference to the preceding figures. The casing has two main faces 25, 26 and an edge 27. The lid 24 defines, with the base 23, an opening 28 on the edge 27. The opening 28 is oriented so that the emanations when leaving the support are not aimed directly towards the nostrils and travel a distance before coming in contact with the nostrils or the nasal mucosa. The width of the opening 28 varies as a function of the relative angular position of the base 23 and the lid 24, and the opening 28 is capable of being totally closed off in a storage position. Controlling the width of the opening 28 regulates output rate of the volatile emanations.

The device shown in FIG. 3A is preferably configured to provide a reloadable structure by fitting the lid 24 in a removable manner in relation to the base 23. The support, contained inside the casing, can be made of a material which, in addition to those already mentioned with reference to FIGS. 1A, 1B, 5A, 5B, may be chosen from among wood, felt, wool, cellulose, terracotta, plaster, ceramics, etc.

In the embodiment shown in FIG. 3B, the device comprises a body 20 consisting of two parts 21, 22 formed in one piece. The part 21 essentially comprises the attachment arms 3, 4. The second part 22 forms a recess 30 which includes two main faces 25, 26 and an edge 27. The edge 27 has, opposite the free end 5, 6 of the arms 3, 4, an opening 31 intended for introducing a support 2 of the type described with reference to the preceding figures. The support 2 for the embodiment of FIG. 3B preferably has two layers 34, 35, each one containing an active substance or different scent. The two layers 34, 25 may be attached to one another by adhesive bonding, or may be free, thereby defining two separate supports. Each of the faces 25, 26 has an opening 32, 33 which, before the first use, may be closed off by a peelable occlusive film. During use, after the support 2 has been inserted into the recess 30, the user removes one and/or the other of the occlusive films, in such a way as to permit diffusion through one and/or the other of the openings 32, 33, so as to permit inhalation of one or other of the active substances or scents, or a cocktail of the two. Thus, the diffusion takes place either through the opening 31 oriented opposite (away from) the nostrils, or through one and/or the other of the openings 32, 33 oriented perpendicular to the nostrils when the device is attached in the manner represented in FIG. 2. Once again, no emanation is oriented directly opposite (i.e., aimed directly towards) the nostrils.

Figure 6:
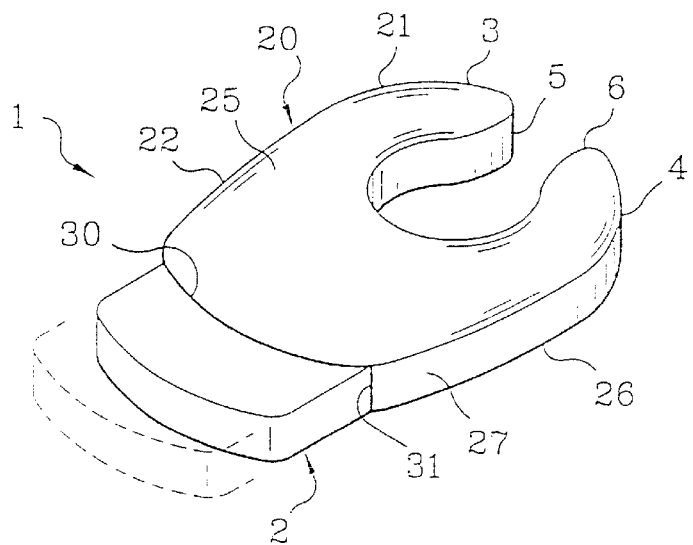
FIG. 6 is a view similar to FIG. 6 showing a sixth embodiment of the device.

In the embodiment shown in FIG. 6, the recess 30 has a single opening 31 on the edge 27. The opening 31 has a width substantially identical to the width of the support 2 to allow the support 2 to be inserted by force through the opening 31. During use, the user inserts the support 2 to a greater or lesser extent into the recess 30 in such a way as to act on the output rate of the emanations. For example, the output rate is lower when the support 2 is inserted further into the recess 30. As shown in FIG. 6, the output rate (diffusion) of the emanations are reduced when the support 2 is moved from the position illustrated in broken lines to the position illustrated in unbroken lines. Similar to the other embodiment, the emanations are not oriented directly opposite (i.e., not aimed directly towards) the nostrils.

It will be apparent to those skilled in the art that various modifications and variations can be made to the structure and methodology of the present invention without departing from the scope or spirit of the invention. In view of the foregoing, it is intended that the present invention cover modifications and variations of this invention provided they fall within the scope of the following claims and their equivalents.

What is claimed is:

1. An inhalation device comprising:

a body;

at least one support removably received in the body, the support containing a product including at least one active substance, the support being able to release, in the form of emanations, a volatile phase of the at least one active substance; and attachment elements permitting attachment of the device to at least one point situated near the nostrils to permit nasal inhalation of the emanations, the at least one support and the attachment elements being configured so that the emanations when leaving the support are not aimed directly towards the nostrils and travel a distance before coming in contact with the nostrils or the nasal mucosa, wherein the body is made of a material impervious to the emanations, the attachment elements being at least one portion of the body, wherein the body has a recess capable of receiving the support and at least one opening to allow the emanations to pass from the recess, wherein the body includes a first face having a first opening formed therein and a second face, opposite to the first face, having a second opening formed therein, and wherein the support includes at least first and second superposed layers, the first layer having a first active substance capable of diffusing through the first opening and the second layer having a second active substance capable of diffusing through the second opening.

2. An inhalation device comprising:

a body;

at least one support removably received in the body, the support containing a product including at least one active substance, the support being able to release, in the form of emanations, a volatile phase of the at least one active substance; and attachment elements permitting attachment of the device to at least one point situated near the nostrils to permit nasal inhalation of the emanations, the at least one support and the attachment elements being configured so that the emanations when leaving the support are not aimed directly towards the nostrils and travel a distance before coming in contact with the nostrils or the nasal mucosa, wherein the body is made of a material impervious to the emanations, the attachment elements being at least one portion of the body, wherein the body has a recess capable of receiving the support and at least one opening to allow the emanations to pass from the recess, wherein the body includes a first face having a first opening formed therein and a second face, opposite to the first face, having a second opening formed therein, and wherein the device further comprises a first support having a first active substance capable of diffusing through the first opening and a second support having a second active substance capable of diffusing through the second opening.

* * * * *